United States Patent
Kovalsky et al.

(10) Patent No.: US 9,192,466 B2
(45) Date of Patent: Nov. 24, 2015

(54) MITRAL BIOPROSTHESIS WITH LOW VENTRICULAR PROFILE

(75) Inventors: Igor Kovalsky, Mounds View, MN (US); Cynthia Clague, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 614 days.

(21) Appl. No.: 13/278,050

(22) Filed: Oct. 20, 2011

(65) Prior Publication Data

US 2012/0101572 A1  Apr. 26, 2012

Related U.S. Application Data (60) Provisional application No. 61/405,370, filed on Oct. 21, 2010.

(51) Int. Cl.
*A61F 2/24* (2006.01)
*A61F 2/82* (2013.01)

(52) U.S. Cl.
CPC ....... *A61F 2/2418* (2013.01); *A61F 2220/0016* (2013.01); *A61F 2230/008* (2013.01); *A61F 2230/0013* (2013.01); *A61F 2230/0054* (2013.01); *A61F 2250/0039* (2013.01); *A61F 2250/0063* (2013.01)

(58) Field of Classification Search
CPC . A61F 2/24; A61F 2/2418; A61F 2220/0016; A61F 2250/0039
USPC ............... 623/1.24, 1.26, 2.1, 2.12–2.19, 1.3, 623/1.31
See application file for complete search history.

(56) References Cited

U.S. PATENT DOCUMENTS

| | | | |
|---|---|---|---|
| 7,569,071 B2 * | 8/2009 | Haverkost et al. ........... 623/1.24 |
| 2003/0036791 A1 | 2/2003 | Philipp et al. |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0208328 A1 | 8/2008 | Antocci et al. |
| 2008/0255660 A1 | 10/2008 | Guyenot et al. |
| 2008/0255661 A1 | 10/2008 | Straubinger et al. |
| 2009/0005863 A1 | 1/2009 | Goetz et al. |
| 2009/0216310 A1 | 8/2009 | Straubinger et al. |
| 2009/0216312 A1 | 8/2009 | Straubinger et al. |

(Continued)

FOREIGN PATENT DOCUMENTS

WO   WO2004/019825   3/2004

*Primary Examiner* — Brian Pellegrino (57) ABSTRACT

A heart valve prosthesis configured for placement at a mitral valve in the heart is disclosed that includes a stent-like support structure for supporting a prosthetic mitral valve. The support structure is configured to have a low ventricular profile with only a short length thereof protruding into the left ventricle when deployed in vivo. The support structure includes an upstream section that is outwardly expandable to sit against the atrial wall so as to at least partially anchor the prosthesis therein and a downstream section to which the prosthetic mitral valve is coupled that extends between the left atria and ventricle through the native mitral valve. The low-ventricular profile of the prosthesis is achieved by shaping the support structure such that the downstream section extends within and overlaps with the upstream section at given regions around the circumference of the support structure in an expanded configuration.

17 Claims, 4 Drawing Sheets

(56) References Cited

U.S. PATENT DOCUMENTS

2009/0216313 A1  8/2009  Straubinger et al.
2009/0276040 A1  11/2009  Rowe et al.
2010/0030330 A1  2/2010  Bobo et al.
2010/0217382 A1  8/2010  Chau et al.

* cited by examiner

MITRAL BIOPROSTHESIS WITH LOW VENTRICULAR PROFILE

CROSS REFERENCE TO RELATED APPLICATION

This application claims benefit under 35 U.S.C. §119(e) to U.S. Appl. No. 61/405,370, filed Oct. 21, 2010, which is incorporated by reference herein in its entirety.

FIELD OF THE INVENTION

The invention relates generally to a prosthetic valve for replacing a native or previously implanted prosthetic valve in a non-surgical interventional procedure. More particularly, the invention relates to apparatus and methods associated with prosthetic heart valves.

BACKGROUND OF THE INVENTION

The mitral valve exhibits two types of pathologies: regurgitation and stenosis. Regurgitation is the more common of the two defects. Either defect may be treated by a surgical repair. Under certain conditions, the mitral valve must be replaced. A standard surgical approach to mitral valve replacement requires cutting open the left side of the heart to access the native mitral valve.

US 2008/0071363 to Tuval et al, describe prosthesis for implantation at a native semilunar valve of a native valve complex via in at least one embodiment a transapical approach. The prosthesis includes a distal fixation member, configured to be positioned in a downstream artery, and shaped so as to define exactly three proximal engagement arms that are configured to be positioned at least partially within respective ones of semilunar sinuses, and, in combination, to apply, to tissue that defines the semilunar sinuses, a first axial force directed toward a ventricle. The prosthesis further includes a proximal fixation member configured to be positioned at least partially on a ventricular side of the native semilunar valve, and to apply, to the ventricular side of the native valve complex, a second axial force directed toward the downstream artery, such that application of the first and second forces couples the prosthesis to the native valve complex.

US 2009/0276040 to Rowe et al. describe a prosthetic mitral valve assembly and method of inserting the same via in at least one embodiment a transapical approach. In certain embodiments, the prosthetic mitral valve assembly includes a stent or outer frame having a flared upper end and a tapered portion to fit the contours of the native mitral valve.

US 2010/0217382 to Chau et al. describe a prosthetic mitral valve assembly and method of inserting the same via in at least one embodiment a transapical approach. The prosthetic mitral valve assembly includes a stent frame and valve combination with an upper anchoring portion being positionable above the annulus of the mitral valve within the left atrium. The upper anchoring portion of the stent frame may include a lattice structure with cells left intentionally disconnected from adjacent cells and bent outwardly to create prongs for anchoring the valve assembly.

US 2009/0005863 to Goetz et al. describe a replacement valve for implantation centrally within the orifice of a malfunctioning native heart valve. The valve is designed for minimally invasive entry through an intercostal opening in the chest of a patient and an opening in the apex of the human heart. The replacement valve includes either a separate anchor or a combined anchor that folds around the malfunctioning native valve leaflets, sandwiching them in a manner so as to anchor the replacement valve at a desired location.

US 2009/0216312 to Straubinger et al. describe a stent for the positioning and anchoring of a valvular prosthesis in an implantation site in the heart of a patient. Specifically, Straubinger relates to an expandable stent for an endoprosthesis having positioning arches and retaining arches, whereby at least one positioning arch is connected to at least one retaining arch via a first connecting web. The stent also includes at least one auxiliary retaining arch that connects the respective arms of the at least one retaining arch connected to the at least one positioning arch.

US 2008/0255660 to Guyenot et describe a medical device for treating a heart valve insufficiency with an endoprosthesis that can be introduced into a patient's body and expanded to secure a heart valve prosthesis in the patient's aorta. The endoprosthesis may have a plurality of positioning arches configured to be positioned with respect to a patient's aorta connected to and positioned above a plurality of retaining arches to support a heart valve prosthesis.

Due to the different physical characteristics of the mitral valve as compared to other valves such as the pulmonary and aortic valves, percutaneous implantation of a prosthetic valve in the mitral position has its own unique requirements for valve replacement. There is a continued need within the art to provide improved mitral valve replacement devices that may be delivered by minimally invasive techniques and that accommodate the structure of the heart.

BRIEF SUMMARY OF THE INVENTION

Embodiments hereof relate to heart valve prosthesis configured for placement at a mitral valve in the heart that include stent-like support structures for supporting a prosthetic mitral valve. The support structures are configured to have a low ventricular profile with only a short length thereof protruding into the left ventricle when deployed in vivo. The support structures include an upstream section that is outwardly expandable to sit against the atrial wall when deployed so as to at least partially anchor the prosthesis therein and a downstream section to which the prosthetic mitral valve is coupled. The downstream section is configured to extend between the left atria and left ventricle through the native mitral valve annulus with the low-ventricular profile of the prosthesis being achieved by shaping the support structure such that the downstream section extends within and overlaps with the upstream section of the support structure at given regions around the circumference of the support structure in a deployed, expanded configuration.

BRIEF DESCRIPTION OF THE DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF EMBODIMENTS OF THE INVENTION

Specific embodiments of the present invention are now described with reference to the figures. The terms "upstream" and "downstream" are used in the following description with respect to a position or direction relative to blood flow through the heart. In addition, as used herein, the terms "outward" or "outwardly" refer to a position radially away from a longitudinal axis LA of the prosthesis while the terms "inward" or "inwardly" refer to a position radially toward a longitudinal axis LA of the prosthesis. In addition, when the term "self-expanding" is used in the following description with reference to the support structure of the valve prosthesis it is intended to convey that the support structure is shaped or formed from a material that has a mechanical memory to return to an expanded deployed configuration from a compressed or constricted delivery configuration. Non-exhaustive exemplary self-expanding materials include stainless steel, a pseudo-elastic metal such as a nickel titanium alloy or Nitinol, a polymer, or a so-called super alloy, which may have a base metal of nickel, cobalt, chromium, or other metal. Mechanical memory may be imparted to a wire or tubular structure by thermal treatment to achieve a spring temper in stainless steel, for example, or to meta shape memory in a susceptible metal alloy, such as nitinol. Various polymers that can be made to have shape memory characteristics may also be suitable for use in embodiments hereof to include polymers such as polynorborene, trans-polyisoprene, styrene-butadiene, and polyurethane. As well poly L-D lactic copolymer, oligo caprytactone copolymer and poly cyclo-octine can be used separately or in conjunction with other shape memory polymers.

In other embodiments in accordance herewith, the support structure of the valve prosthesis may be made of a shape memory biodegradable material, such as a natural or synthetic biodegradable polymer, non-limiting examples of which include polysaccharides such as alginate, dextran, cellulose, collagen, and chemical derivatives thereof, proteins such as albumin, zein and copolymer blends thereof, alone or in combination with synthetic polymers, polyhydroxy acids, such as potylactides, polyglycolides and copolymers thereof, poly(ethylene terephthalate), poly(hydroxybutyric acid); poly(hydroxyvaleric acid), poly[lactide-co-(ε-caprolactone)]; poly[glycolide-co-(ε-caprolactone)], polycarbonates, poly(pseudo amino acids); poly(amino acids); poly(hydroxyalkanoate)s, polyanhydrides; polyortho esters, and blends and copolymers thereof.

The following detailed description is merely exemplary in nature and is not intended to limit the invention or the application and uses of the invention. Although the description of the invention is in the context of treatment of heart valves such as the mitral valve, the invention may also be used in any other body passageway's where it is deemed useful. Furthermore, there is no intention to be bound by any expressed or implied theory presented in the preceding technical field, background, brief summary or the following detailed description.

Figure 1:
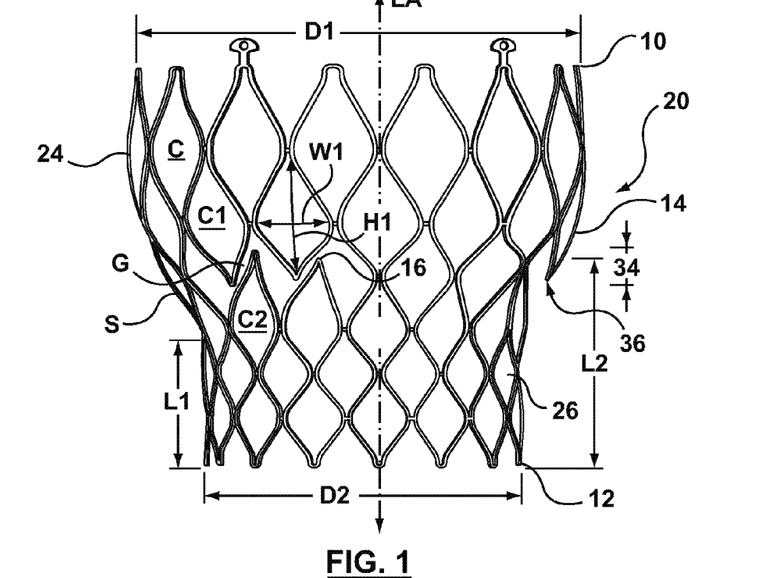
FIG. 1 is a schematic side view of a support structure of a mitral valve bioprosthesis, the support structure being shaped to define continuous regions and discontinuous regions in accordance with an embodiment hereof.

Embodiments hereof are related to a valve prosthesis configured for placement at a mitral valve in the heart to lie between the left atrium and the left ventricle. FIG. 1 depicts a support structure 20 of a mitral valve bioprosthesis 22 in an expanded configuration in accordance with an embodiment hereof. Support structure 20 is a self-expanding stent-like framework having a stepped expanded profile with an upstream end 10 having an expanded diameter D1 and a downstream end 12 having an expanded diameter D2 that is less than expanded diameter D1. The stent-like framework defines cells C of a diamond-like shape but other cell shapes are contemplated without departing from the scope hereof. Support structure 20 with a prosthetic valve attached thereto may be radially compressed within a sheath or other containment structure of a catheter-based delivery system for tracking to a treatment site within the heart and returns to the expanded configuration shown in FIG. 1 due to the self-expanding property of the structure.

Figure 2:
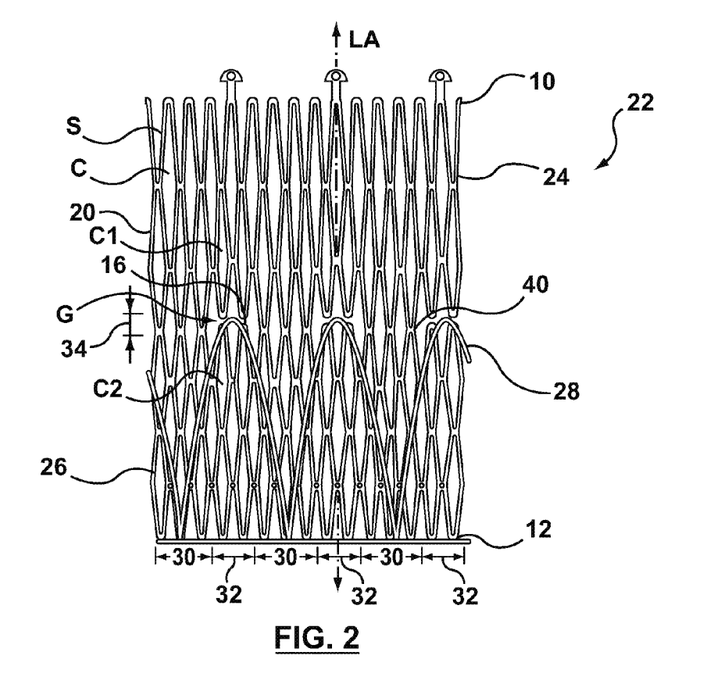
FIG. 2 is a schematic of a flattened unexpanded support structure in accordance with FIG. 1 overlaid with the outline of a prosthetic mitral valve in accordance with an embodiment hereof.

FIG. 2 shows support structure 20 flattened, i.e., not yet formed into a tubular shape, and overlaid with the outline of a prosthetic mitral valve 28. The stent-like framework of support structure 20 is formed by a plurality of struts S that define cells C in a mesh or net pattern that has continuous regions 30 and discontinuous regions 32. A continuous region 30 of support structure 20 may be described as forming a longitudinally extending band or strip of cells C that are continuously connected one to the other from upstream end 10 to downstream end 12 of the support structure. A discontinuous region 32 of support structure 20 may be described as forming a longitudinally extending band or strip of cells C that have a set or pair of longitudinally adjacent or neighboring cells, for example downstream cell C1 of upstream section 24 and corresponding upstream cell C2 of downstream section 26, that are not connected to each other such that a break or gap G exists therein. Continuous regions 30 and discontinuous regions 32 alternate with one another around a circumference of support structure 20, as shown in FIGS. 1 and 2, and define a circumferential a transitional or joint segment 34 that encompasses the circumferential portion of support structure 20 where a set or group of not connected or discontinuous cells are separated by a set or a group of connected or continuous cells.

Support structure 20 essentially divides at joint segment 34 into an upstream section 24 and a downstream section 26 with the discontinuities or gaps within joint segment 34 allowing the joined or connected cells within the segment to act as hinges at which upstream section 24 curves outwardly to transition from substantially cylindrical downstream section 26 when in an expanded configuration. In embodiments hereof, the aforementioned hinging facilitates delivery of the bioprosthesis, for example, transseptally, by providing the bioprosthesis with a small crimp profile as well as increased flexibility in a delivery configuration.

Upstream section 24 has expanded diameter D1 from upstream end 10 of support structure 20 to an inwardly curved end 14 at joint segment 34, while downstream section 26 has expanded diameter D2 from downstream end 12 of support structure 20 to interior ends 16 at joint segment 34. Within each discontinuous region 32, downstream section 26 has along segment of a length L2 that extends from a respective interior end 16 to support structure downstream end 12. Downstream section 26 also has multiple short segments of a length L1 that substantially extend from the curved portion or upstream section 24 to support structure downstream end 12, an arrangement that may be understood by a comparison of FIGS. 1 and 3 with FIGS. 2 and 4, respectively.

Figure 3:
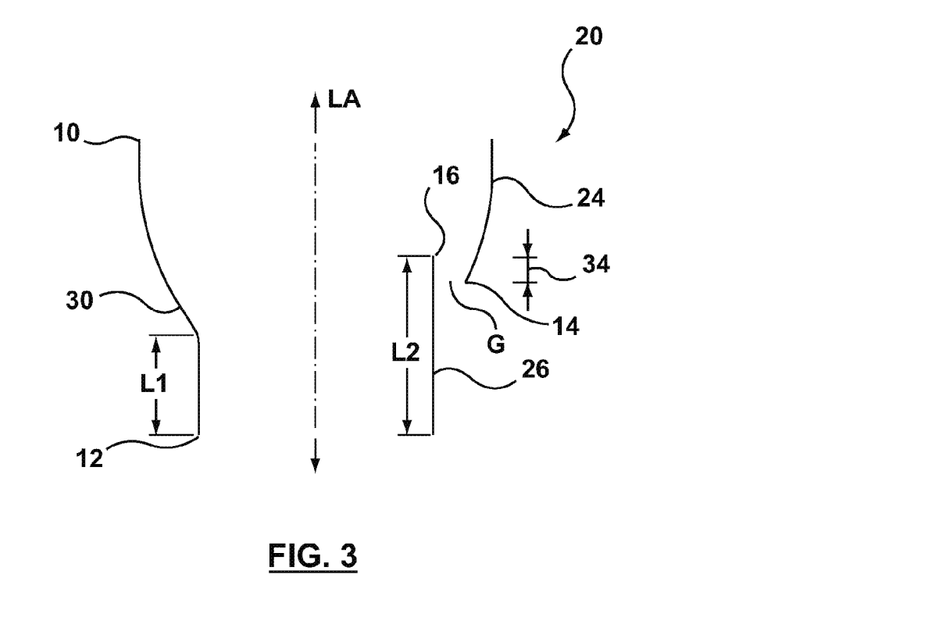
FIG. 3 is a schematic sectional view of the support structure of FIG. 1.
Figure 4:
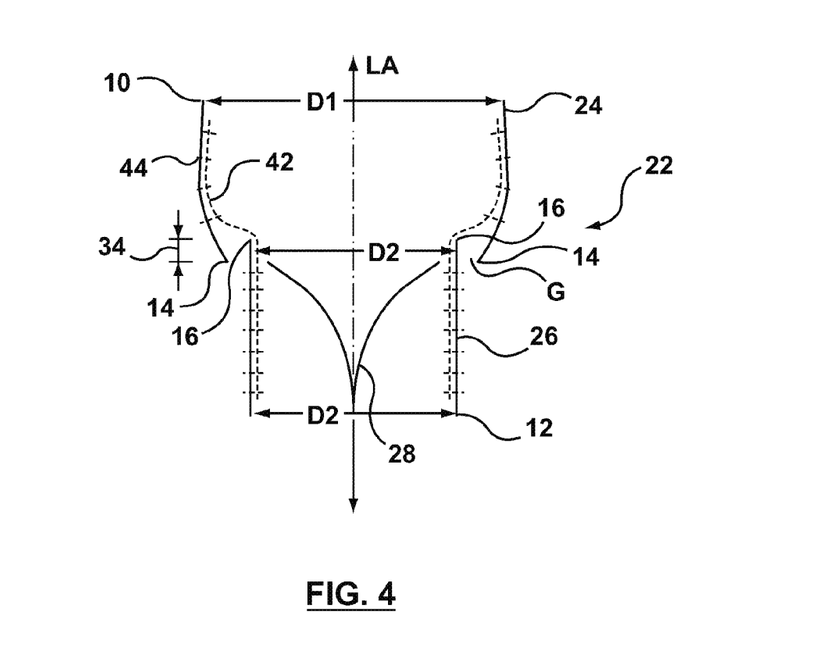
FIG. 4 is a schematic sectional view of the support structure of FIG. 1 with a lining disposed inside the support structure in accordance with an embodiment hereof.
Figure 5A:
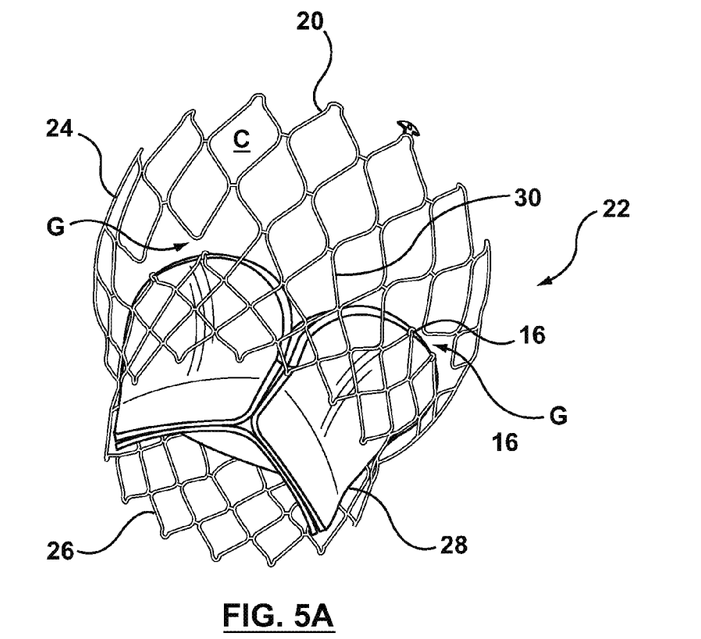
FIG. 5A is a perspective view of the support structure of FIG. 1 with a prosthetic mitral valve disposed therein in accordance with an embodiment hereof.
Figure 5B:
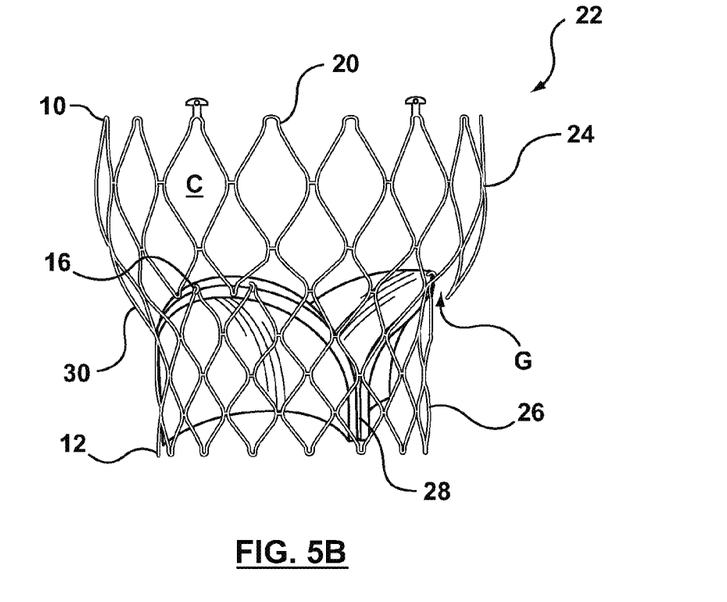
FIG. 5B is a side view of the support structure of FIG. 1 with a prosthetic mitral valve disposed therein in accordance with an embodiment hereof.
Figure 5C:
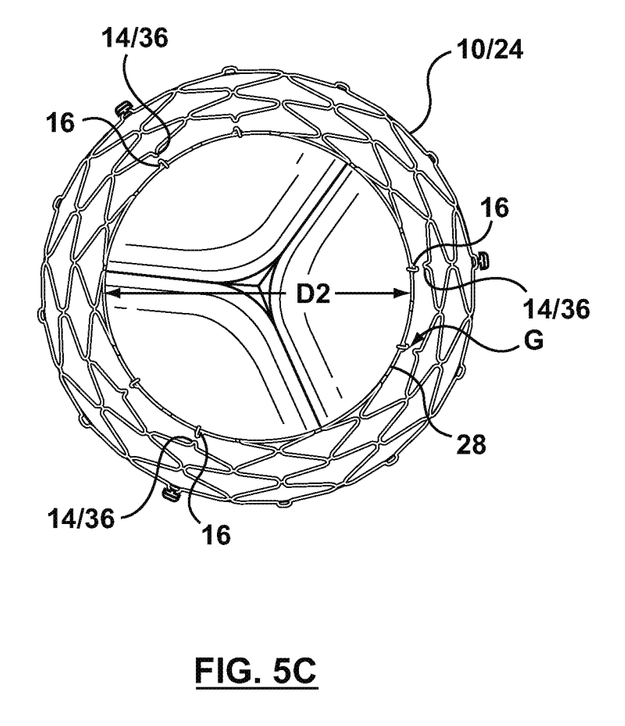
FIG. 5C is an upstream end view of the support structure with the prosthetic mitral valve disposed therein shown in FIG. 5B.

As noted above, inwardly curved end 14 of upstream section 24 and interior ends 16 of downstream section 26 occur within joint segment 34 of support structure 20. More particularly, within discontinuous regions 32 when support structure 20 is in the expanded state as shown in FIGS. 1, 3 and 4, interior ends 16 of downstream section 26 are positioned upstream and radially inward of inwardly curved end 14 of upstream section 24 to extend within an interior of upstream section 24 such that downstream section 26 of support structure 20 in an expanded state may be considered to have portions that overlap with upstream section 24 of support structure 20. Described in another manner, within discontinuous region 32 when support structure 20 is in the expanded state representative upstream cell C2 of downstream section 26 at least partially extends within and is positioned radially inward of representative downstream cell C1 of upstream section 24 to create the overlap of the upstream and downstream sections. This overlapping arrangement desirably minimizes the ventricular profile of mitral valve bioprosthesis 22, i.e., minimizes the extent to which the bioprosthesis will protrude into a patient's left ventricle outflow tract. In an embodiment, support structure 20 is configured to have a low ventricular profile such that only a length of less than 15 mm thereof protrudes into the left ventricle when deployed in vivo. In another embodiment, support structure 20 is configured to have a low ventricular (profile such that only a length of less than 12 mm thereof protrudes into the left ventricle when deployed in vivo.

When deployed within the heart, upstream section 24 is of a length and diameter to be fully disposed within the left atrium with downstream section 26 being of a length and diameter to extend from within the left atrium to the left ventricle of the heart through the native mitral valve annulus with only length L1 of downstream section 26 extending into the left ventricle. More particularly, upstream section 24 is sized to radially expand into contact with the walls of the atrium that surround the native mitral valve so as to at least partially anchor mitral valve bioprosthesis 22 therein, whereas downstream section 26 is sized to radially expand to a generally cylindrical or tubular expanded configuration that fits through the native mitral valve annulus and that supports a deployed diameter of a prosthetic mitral valve 28 secured thereto with length L1 extending into the left ventricle.

As illustrated in FIGS. 2, 4 and 5A-5C, prosthetic mitral valve 28 is coupled to downstream section 26 of support structure 20. Prosthetic mitral valve 28 is a tricuspid valve with three curved leaflets. Each leaflet is sewn at its most upstream point of curvature, i.e., at the nadir of the valve leaflet, to a respective interior end 16 of downstream section 26. The remainder of each curved leaflet extends along downstream section 26 to downstream end 12 and is correspondingly sewn to the stent-like framework such that when mitral valve bioprosthesis 22 is expanded, prosthetic mitral valve 28 is permitted to unfold to its fully deployed diameter. In embodiments hereof, support structure 20 may be dimensioned such that diameter D2 of downstream section 26 is at or between 25 and 35 mm with length L1 of the downstream base portion of downstream section 26 being at or between 8 and 13 mm and length L2 of downstream section 26 at interior ends 16 being at or between 14 and 18 mm and may accommodate a prosthetic mitral valve having an effective diameter of approximately 30 mm. In accordance with embodiments hereof, length L2 to L1 may be a ratio of 5:4 and more particularly may be a ratio of 4:3.

In accordance with embodiments hereof and with reference to FIG. 2, support structure 20 may be cut from a single piece or sheet of metallic or polymeric material. As shown, within continuous regions 30, the struts of the support structure form cells that are continuous, and within discontinuous regions 32, there is a gap between a pair of adjacent cells defined by the struts. Accordingly support structure 20 may be laser cut from a solid component of self-expanding material such that it is an integral structure that does not include individual components. A single integral structure allows the support structure to be crimped or compressed to a low delivery profile. Alternatively, rather than being laser cut, the support structure 20 may be formed using any of a number of different methods that would be apparent to one of ordinary skill in the art such as connecting individual annular, stent struts together, chemical etching, or another method of cutting a desired shape from a solid component.

In embodiments hereof, shaping support structure 20 to have discontinuities or gaps between upstream section 24 and downstream section 26 results in a mechanical decoupling between the upstream and downstream sections of bioprosthesis 22, i.e., the shaping of support structure 20 permits upstream section 24 and downstream section 26 to be formed to have different, respective properties. In an alternate embodiment, apparatus and methods described herein may be applied to a support structure that includes an upstream section and a downstream section that are cut from separate pieces of metal, and that are coupled to one another. In another embodiment, an integral or multi-piece support structure 20 may have a downstream section 26 that is shaped so as to provide a stiff frame for supporting prosthetic valve 28 in order to provide fatigue resistances to this segment of the support structure. In another embodiment, an integral or multi-piece support structure 20 may have upstream section 24 that is shaped on as to be flexible in order to facilitate conformation of the upstream section to the left atrial watt upon deployment of bioprosthesis 22 in vivo.

Although bioprosthesis 22 is shown in FIG. 2 as including a trileaflet valve, the apparatus and techniques described herein can be adapted to a prosthetic bileaflet valve. For a prosthetic trileaflet valve, as shown, support structure 20 is shaped such that three discontinuous regions are at equidistant locations around the circumference of the support structure 20 with gaps G between neighboring cells of the upstream and downstream sections 24, 26 having three sets of interior ends 16 wherein each set is for attachment to a nadir of a corresponding curved leaflet of the prosthetic trileaflet valve as described above. In the embodiment shown, out of a total of fifteen cell junctions 40 within joint segment 34 around the circumference of support structure 20, six of the cell junctions 40 are not connected or in other words are discontinuous.

In an embodiment, the cells of upstream section 24 that are adjacent to gaps G in support structure 20 may act as barbs 36. Use of such barbs 36 prevents downstream migration of bioprosthesis 22 into the left ventricle by becoming anchored to tissue in the vicinity of the native mitral valve within the left atrium. In embodiments hereof, the characteristics of barbs 36 may depend on a width W1 and a height H1 of the cell that forms the barb, as well as the inward curvature of the cell, as depicted in FIG. 1.

With further reference to FIG. 4, support structure 20 may include a lining 42 disposed inside thereof in accordance with an embodiment hereof. Lining 42 may be placed inside or along an interior surface of support structure 20, for e.g., attached to support structure 20 via sutures 44, such that lining 42 lines gaps G within the discontinuous regions 32 thereof to provide a smooth flow surface and/or prevent stagnation of the blood, which may otherwise develop within discontinuous regions 32. In an embodiment, lining 42 may cover an interior surface of support structure 20 only in an area of the support structure where downstream section 26 overlaps with upstream section 24 to provide a smooth flow surface and/or prevent stagnation of the blood in that area of the support structure. In embodiments in accordance herewith, lining 42 is a biocompatible material and may be a low-porosity woven fabric, such as polyester, Dacron fabric, or PTFE, which creates a one-way fluid passage when attached to the support structure. In one embodiment, the lining may be a knit or woven polyester, such as a polyester or PTFE knit, which can be utilized when it is desired to provide a medium for tissue ingrowth and the ability for the fabric to stretch to conform to a curved surface. Polyester velour fabrics may alternatively be used, such as when it is desired to provide a medium for tissue ingrowth on one side and a smooth surface on the other side. These and other appropriate cardiovascular fabrics are commercially available from Bard Peripheral Vascular, Inc. of Tempe, Ariz., for example. In another embodiment, lining 42 could also be a natural material such as pericardium or another membranous tissue such as intestinal submucosa It is noted that although downstream section 26 of support structure 20 of bioprosthesis 22 is described hereinabove as being generally cylindrical, embodiments in accordance herewith include a support structure having a downstream section that flares outwardly at a downstream end thereof.

Natural tissue for replacement valve leaflets for use in prosthetic mitral valves in accordance with embodiments hereof may be obtained from, for example, heart valves, aortic roots, aortic walls, aortic leaflets, pericardial tissue, such as pericardial patches, bypass grafts, blood vessels, intestinal submucosal tissue, umbilical tissue and the like from humans or animals such as from bovine or porcine origins. Synthetic materials suitable for use herein may include DACRON® polyester commercially available from Invista North America S.A.R.L. of Wilmington, Del., other cloth materials, nylon blends, polymeric materials, and vacuum deposition nitinol fabricated materials. One polymeric material from which the leaflets can be made is an ultra-high molecular weight polyethylene material commercially available under the trade designation DYNEEMA from Royal DSM of the Netherlands. With certain prosthetic leaflet materials, it may be desirable to coat one or both sides of the leaflet with a material that will prevent or minimize overgrowth. It is further desirable that the prosthetic leaflet material is durable and not subject to stretching, deforming, or fatigue.

Mitral valve bioprosthesis in accordance with embodiments hereof may be deployed within a native mitral valve or previously implanted prosthetic valve via a suitable catheter-based delivery system, such as the Medtronic CoreValve® delivery system with AccuTrak™ Stability Layer and the Engager™ Transcatheter Aortic Valve Implantation System, each of which is a heart valve delivery system developed by Medtronic, Inc. of Minneapolis, Minn. that may be adapted for use in embodiments hereof. Mitral valve bioprosthesis accordance with embodiments hereof may be positioned or tracked to the deployment site within the heart by any one of a suitable transfemoral, transapical, transseptal and transatrial approach as may be preferred and selected by a particular clinician.

While various embodiments according to the present invention have been described above, it should be understood that they have been presented by way of illustration and example only, and not limitation. It will be apparent to persons skilled the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A valve prosthesis configured for percutaneous deployment at a mitral valve in the heart, the prosthesis comprising:
a support structure configured to support a prosthetic heart valve, wherein the support structure has a stent framework having an upstream section with a greater expanded diameter than a downstream section, and defining a plurality of continuous regions and a plurality of discontinuous regions that alternate with one another around a circumference of the stent framework,
wherein each of the continuous regions of the stent framework forms a longitudinally extending band of cells that are connected to each other from an upstream end to a downstream end of the stent framework, and wherein each of the discontinuous regions of the stent framework forms a longitudinally extending band of cells from the upstream end to the downstream end of the stent framework with neighboring cells between the upstream and downstream sections being unconnected from one and other, and
wherein within each of the discontinuous regions of the stent framework the unconnected cell of the downstream section at least partially overlaps with the unconnected cell of the upstream section by longitudinally extending within the upstream section of the stent framework such that the unconnected cell of the downstream section is positioned radially inward of the unconnected cell of the upstream section.

2. The valve prosthesis of claim 1, wherein struts of the stent framework define the cells of the continuous and discontinuous regions.

3. The valve prosthesis of claim 1, wherein the unconnected cell of the downstream section forms an upstream interior end of the downstream section within each of the discontinuous regions.

4. The valve prosthesis of claim 3 further comprising:
a prosthetic tricuspid heart valve attached to the downstream section of the stent framework with each of the prosthetic leaflets being attached at its highest point of curvature to a corresponding upstream interior end of the downstream section.

5. The valve prosthesis of claim 3, wherein within each of the discontinuous regions the unconnected cell of the upstream section inwardly curves and is configured to be a barb to secure the support structure upon deployment in vivo.

6. The valve prosthesis of claim 1, wherein the downstream section of the stent framework in an expanded configuration defines a cylinder that includes short segments of a length L1 and long segments of a length L2 that is longer than the length L1.

7. The valve prosthesis of claim 6, wherein the short segments of the downstream section are in the continuous regions of the stent framework and the long segments of the downstream section are in the discontinuous regions of the stent framework to alternate with one another around a circumference of the stent framework.

8. The valve prosthesis of claim 7, wherein the long segments of the downstream section have an upstream interior end that extends inside of the upstream section to create the at least partial overlap between the upstream and downstream sections in each of the discontinuous regions.

9. The valve prosthesis of claim 8 further comprising:
a prosthetic tricuspid heart valve attached to the downstream section of the stent framework with each of the prosthetic leaflets being attached at its highest point of curvature to a corresponding upstream interior end of the downstream section.

10. The valve prosthesis of claim 6, wherein length L2 of the cylinder is between 14 mm and 18 mm and length L1 of the cylinder is between 8 mm and 13 mm.

11. The valve prosthesis of claim 1 further comprising:
a lining secured within the stent framework to provide a smooth flow surface within the discontinuous regions.

12. A valve prosthesis configured for percutaneous deployment at a mitral valve in the heart, the prosthesis comprising:
a support structure configured to support a prosthetic heart valve having an upstream section with a greater expanded diameter than a downstream section, the support structure defining a plurality of cells wherein at spaced locations around a circumference of the support structure the support structure has discontinuous regions in which a cell of the upstream section is detached from a longitudinally adjacent cell of the downstream section, and wherein within each of the discontinuous regions the detached cell of the downstream section of the support structure at least partially overlaps with the detached cell of the upstream section of the support structure by longitudinally extending within the upstream section of the support structure such that the detached cell of the downstream section is positioned radially inward of the detached cell of the upstream section to create the at least partial overlap between the upstream and downstream sections.

13. The valve prosthesis of claim 12, wherein within each of the discontinuous regions the longitudinally adjacent detached cell of the downstream section forms an upstream interior end of the downstream section.

14. The valve prosthesis of claim 13 further comprising:
a prosthetic tricuspid heart valve attached to the downstream section of the support structure with each of the prosthetic leaflets being attached at its highest point of curvature to a corresponding upstream interior end of the downstream section.

15. The valve prosthesis of claim 12, wherein within each of the discontinuous regions the detached cell of the upstream section inwardly curves and is configured to be a barb to secure the support structure upon deployment in vivo.

16. The valve prosthesis of claim 12 further comprising:
a lining secured within the support structure to provide a smooth flow surface therein.

17. The valve prosthesis of claim 16, wherein the lining covers an interior of the support structure where the downstream section of the support structure at least partially overlaps with the upstream section of the support structure to prevent blood stagnation.

* * * * *